Figure 1:
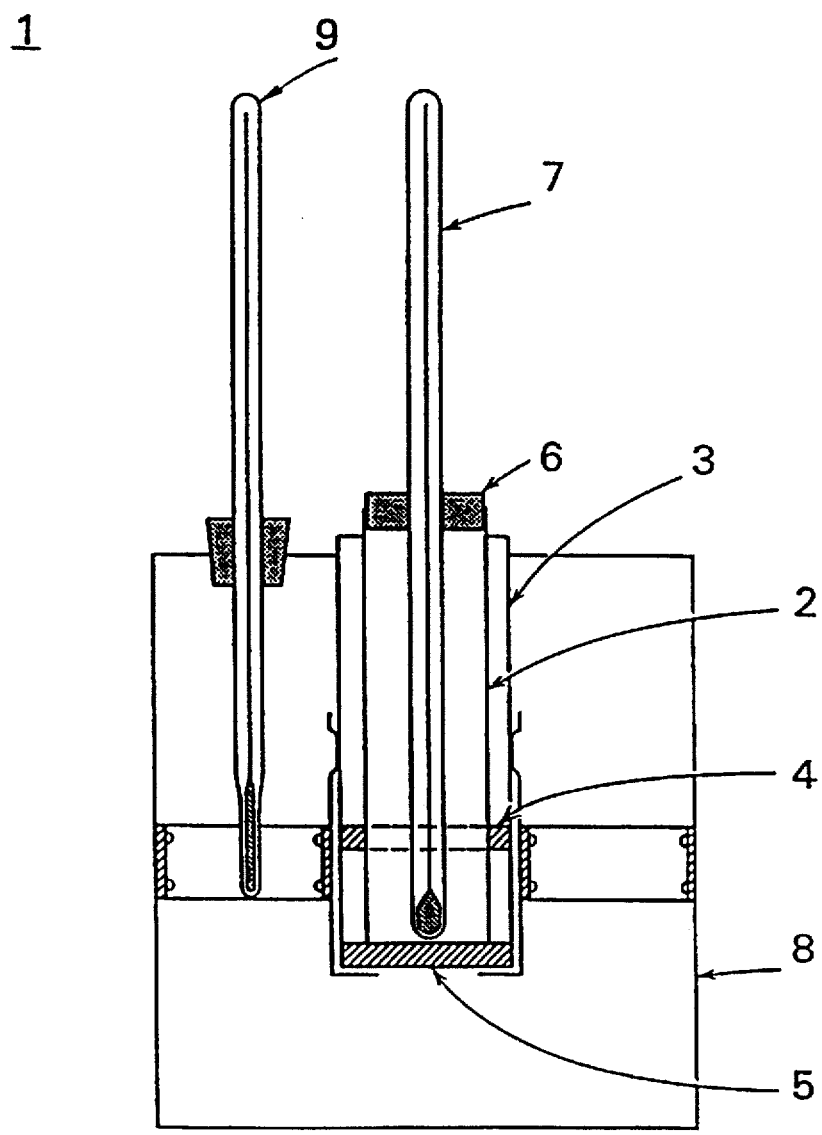

United States Patent [19]

Tolvanen et al.

[11] Patent Number: 5,708,196
[45] Date of Patent: Jan. 13, 1998

[54] METHOD AND APPARATUS FOR DETERMINING THE CLOUD POINT OF OIL

[75] Inventors: Ilkka Tolvanen; Jürg Waldvogel, both of Porvoo; Olli Pilviö, Söderkulla, all of Finland

[73] Assignee: Neste Oy, Espoo, Finland

[21] Appl. No.: 669,461

[22] PCT Filed: Jan. 17, 1995

[86] PCT No.: PCT/FI95/00016

§ 371 Date: Jul. 9, 1996

§ 102(e) Date: Jul. 9, 1996

[87] PCT Pub. No.: WO95/20153

PCT Pub. Date: Jul. 27, 1995

[30] Foreign Application Priority Data

Jan. 19, 1994 [FI] Finland ................... 940260

[51] Int. Cl.⁶ ................... G01N 25/02; G01N 25/14; B03C 5/00

[52] U.S. Cl. ................... 73/53.05; 73/54.42; 73/61.41; 73/61.76

[58] Field of Search ................... 73/53.05, 53.07, 73/54.42, 54.43, 61.41, 61.46, 61.62, 61.76

[56] References Cited

U.S. PATENT DOCUMENTS

| | | | |
|---|---|---|---|
| 2,145,203 | 1/1939 | Walters et al. | 23/230 |
| 2,349,482 | 5/1944 | Welty, Jr. | 73/51 |
| 2,604,392 | 7/1952 | Brown | 73/53 |
| 2,672,751 | 3/1954 | Lupfer et al. | 73/17 |
| 3,143,877 | 8/1964 | Moyer | 73/64 |
| 3,188,857 | 6/1965 | Vesper et al. | 73/53 |
| 3,221,541 | 12/1965 | Osborne | 73/53 |
| 3,779,894 | 12/1973 | Eggen et al. | 208/33 |
| 4,622,119 | 11/1986 | Cerkanowicz et al. | 204/190 |
| 5,222,390 | 6/1993 | Monrabal | 73/61.76 |
| 5,454,257 | 10/1995 | Fotland et al. | 73/61.43 |

OTHER PUBLICATIONS

Tsang et al., "Diesel Cloud Point Determination Needs Uniformity," *Technology—Oil & Gas Journal* pp. 39-43 (1986).

*Primary Examiner*—Hezron E. Williams
*Assistant Examiner*—J. David Wiggins
*Attorney, Agent, or Firm*—Birch, Stewart, Kolasch & Birch, LLP

[57] ABSTRACT

The invention concerns a method and an apparatus for determination of the cloud point of oil. In the method according to the invention the cloud point is determined from a turning point on the oil cooling curve. The method of the invention may be realized in an apparatus comprising a cooling jacket for cooling the oil sample, a measuring space essentially shaped as oppositely located cones, a temperature indicator for determination of the oil cooling curve. With the invention the cloud point of oil can be determined quickly and reliably, the measuring cell of the invention allows a very high degree of exactitude in measurements, the measurement results are well reproducible and the invention makes it possible to bring about a method and an apparatus allowing a fully automatic operating analyzer for determination of the cloud point of oil.

4 Claims, 4 Drawing Sheets

METHOD AND APPARATUS FOR DETERMINING THE CLOUD POINT OF OIL

The invention concerns a method and an apparatus for determining the cloud point of oil. In the method of the invention the cloud point is determined from a turning point on the oil's cooling curve and in an apparatus wherein the oil sample is cooled in a measuring space shaped essentially as cones positioned opposite to one another.

Oil products are mixtures of many different components, and those properties of oil products which restrict their usability are often dependent on the properties of the individual components. One significant factor in particular is the solidification and crystallization of wax components of oil products in a cold climate. In particular, this concerns diesel fuels and fuel oils made of petroleum as well as aviation petroleum. As the operating temperature of oil products drops and wax begins to crystallize in them, this will result in an accumulation of solid wax in various pans of the transportation equipment for these fluids, such as in filters, connection pieces, pumps and burners.

The pour point of an oil product indicates the lowest temperature at which the product in question will flow. Even before this pour point some oil components will crystallize and form a cloud in the product due, among other things, to crystallization of paraffine hydrocarbons. The temperature at which this clouding begins is called the cloud point. The cloud point of oil is the temperature at which paraffin wax or other substances normally dissolved into the oil begin to separate and to form small crystals, thus bringing about clouding in the oil.

The components of an oil product can be influenced by adjusting the refining process, and refineries produce a wide range of oil products having different proportionings of wax, depending on the requirements of the season. For obtaining the desired properties in the refining process the various properties must be measured with sufficient precision. In addition, for controlling the refining process successfully the method of measurement must be quick enough.

The cloud point depends on the components of the oil product just like the other properties of the product: although wax components cause difficulties in cold weather due to crystallization, their energy content is nevertheless good. For this reason, the refining process aims at avoiding any splitting up of wax components as far as possible, whereby the yield of the total refining process will be higher.

An ASTM D 2500 measuring method has been standardized for cloud point determinations. The apparatus to be used in this method is shown in FIG. 1. The determination is based on visual observation of the cloud point. Although the apparatus itself and its dimensions are exactly defined, there is much variation in the obtained measurement results between individual laboratories.

The publication Oil & Gas Journal, Oct. 20, 1986, Technology presents a study in variations in cloud point measurements between different laboratories when using this ASTM method. According to this study, much deviation occurred in the results of cloud point measurements: of 30 values measured at different laboratories only 13 were in the range −29° . . . −31° C., while the extreme values of the measurements were −22° C. and −42° C. respectively.

Thus, a problem with these methods is that the measurement results are too varying or the measuring methods are too slow for adjusting the process.

It has been a problem with known apparatuses that instead of visual observation an optical measuring method has been used in the determination, whereby the results have been greatly different and the moisture content, among other things, disturbs the determination. Additionally, an optical measurement is not at all suitable for naturally opaque oil products.

It is an objective of the present invention to achieve an improvement over known methods for determination of the cloud point of oil. A more specific objective of the invention has been to bring about a method and an apparatus for determination of the cloud point of oil so that the obtained measurement result can be used for controlling the oil quality or for controlling the production.

Another objective of the invention is to bring about a method and an apparatus for an exact, repeatable and prompt determination of the cloud point so that the obtained measurement result can be used for controlling the refining process.

It is an objective of the invention to bring about a method and an apparatus making possible a fully automatically operating analyzer for determination of the cloud point of oil.

Another objective of the invention is to bring about a method and an apparatus for determination of the cloud point also in untransparent or opaque oil products.

The objectives mentioned above have been achieved through a new method and apparatus, the characteristic features of which are presented in the independent claims.

The invention is based on the unexpected finding that the cloud point of oil can be determined quickly and reliably by measuring the cooling curve of the oil and by establishing the cloud point from such a turning point on the cooling curve which is caused by crystallization of products in the oil when such a measuring vessel is used in the measuring apparatus wherein conduction of heat and convection are correctly related.

Another unexpected finding was that when such a measuring vessel is used in the measuring apparatus which is mainly shaped as two oppositely oriented hollow cones disposed to face each other flat base to base along a common bottom perimeter or circumference such that each apex points outwards along a mutual parallel axis of said two cones in an opposite direction, the cloud point could be measured considerably more exactly than with earlier methods and the drawbacks of methods of the prior an could be avoided.

Several advantages are obtained by using a measuring cell in accordance with the invention. A closed sample vessel can be used in it which is remarkably suitable for the conditions prevailing in the process industry. The measuring cell of the invention allows a very high degree of exactness in measurements and the measurement results are highly reproducible, making it suitable as a measurement message required for controlling the production. The invention is suitable for use in a large temperature range and it can be used for measuring the properties of many kinds of oil refinery product, from fuel oil summer grades to arctic grades and aviation petroleum.

The method now developed allows a quick and reliable determination of the cloud point of oil products. The result can be used in oil production control or in oil quality control. An analyzer functioning with the method according to the invention can be fully automated even for sampling and result calculations, which allows the use of an important quality magnitude in the automatic follow-up of the oil production and in process control.

The invention is explained in greater detail by referring to a principal solution of the method according to the invention which is shown in the figures of the appended drawings but to which the invention must not be limited.

FIG. 1. Apparatus for cloud point determination in accordance with ASTM D 2500.

Figure 2:
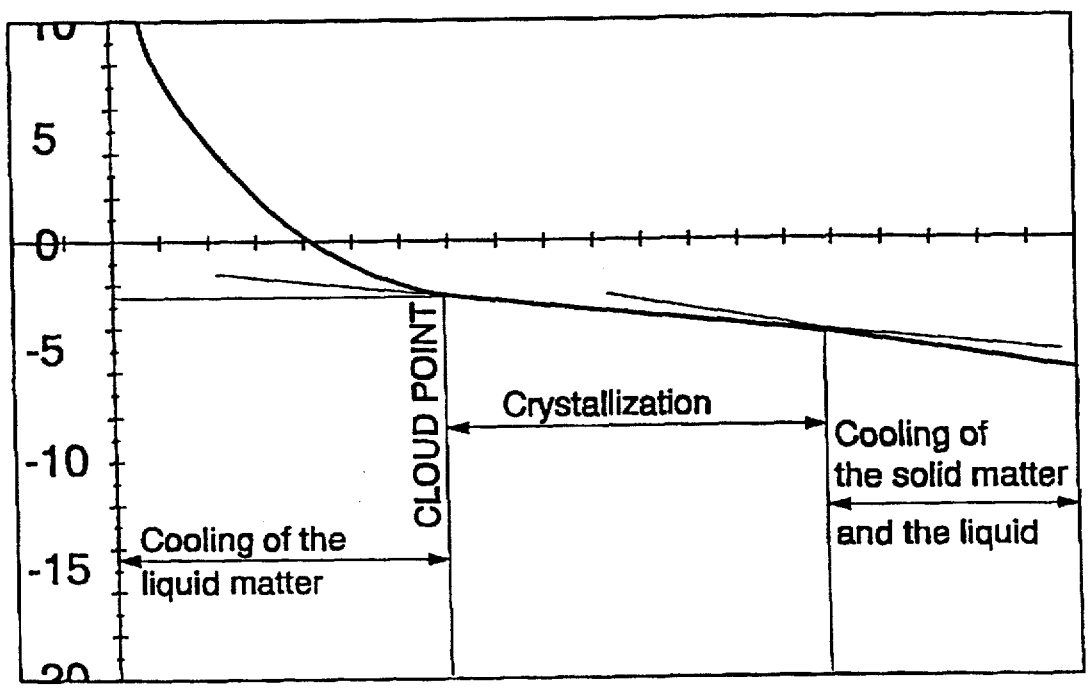

FIG. 2. Oil cooling curve and establishment of the cloud point from a turning point on the cooling curve.

Figure 3:
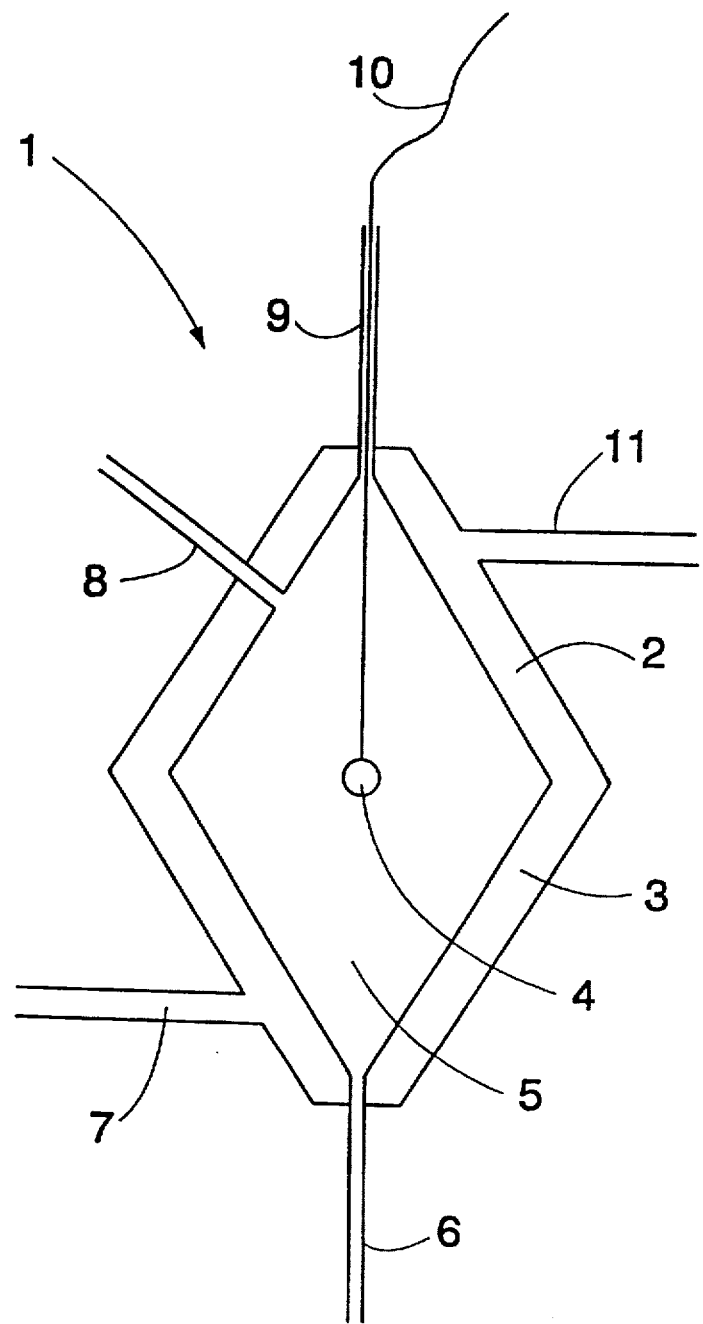

FIG. 3. Measuring vessel in accordance with the invention in an apparatus for cloud point determination.

Figure 4:
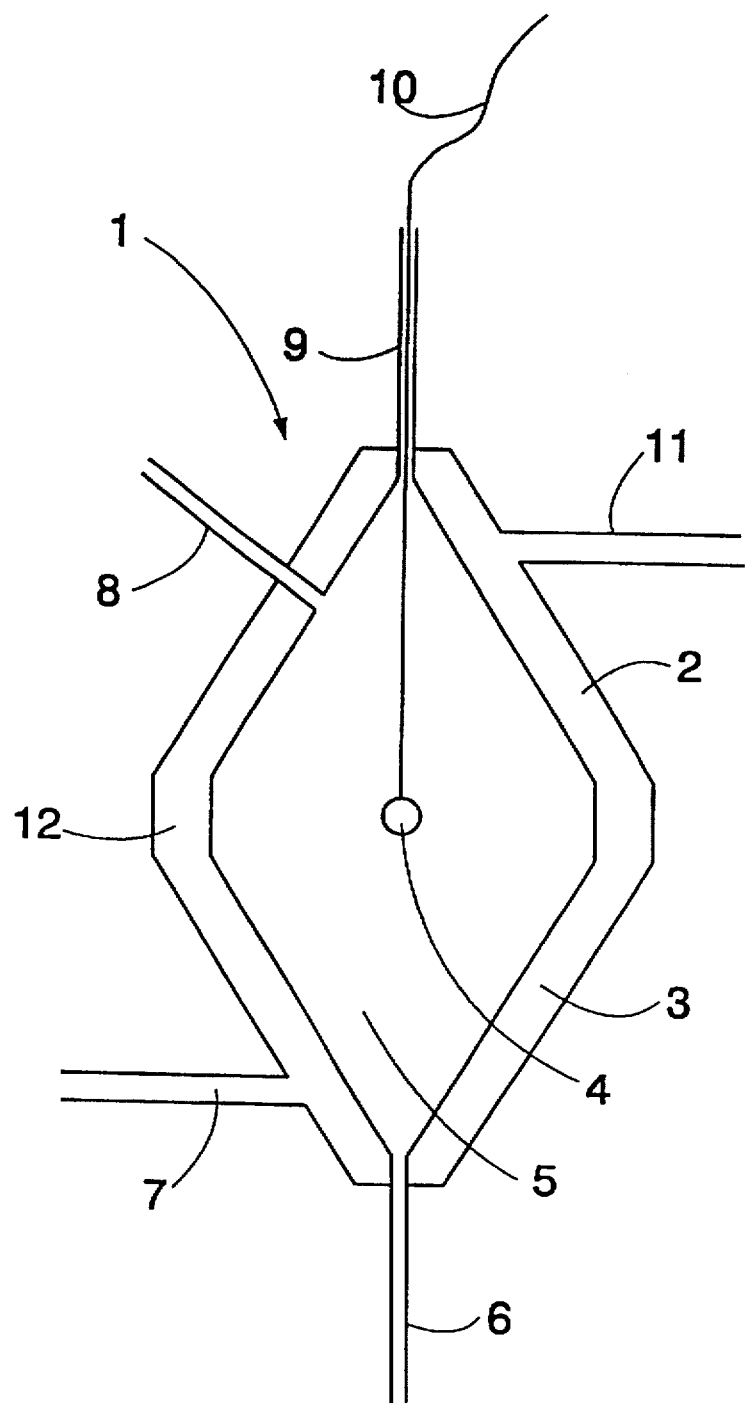

FIG. 4. A variation of the measuring vessel according to the invention in an apparatus for cloud point determination.

FIG. 1 shows an apparatus for cloud point determination in accordance with the ASTM D 2500 standard. Reference number 1 indicates the measuring apparatus generally in the figure. The apparatus comprises measuring tube 2, outer jacket 3 for the measuring tube, sealing ring 4, bottom cork 5 for the measuring tube, cover cork 6 for the measuring tube, thermometer 7, cooling jacket 8 and thermometer 9 for the cold bath. The standard contains more specific provisions regarding the dimensions and raw materials of the measuring apparatus.

With this apparatus the cloud point is determined by placing the oil sample to be examined into measuring tube 2 and by cooling the measuring tube with the aid of cooling jacket 8. By observing the clouding of the oil sample visually the cloud point of the sample is obtained from thermometer 7.

FIG. 2 shows the oil cooling curve and establishment of the cloud point from a turning point on the cooling curve. The curve is obtained by taking a sample into the measuring vessel from the desired oil refining process flow, by cooling the sample through a liquid in the outer jacket and by following the temperature of the sample as a function of time. The measurement result gives the cooling curve shown in FIG. 1. The vertical axis of the graph is the temperature (°C.) and the horizontal axis is time. The first stage in the graph is cooling of the liquid matter, the second stage is crystallization of the liquid components and the third stage is cooling of the solid matter and the liquid. In the graph the cloud point is at a point where the cooling of the liquid matter rams partly into crystallization. By collecting the cooling curve values on a computer it is possible to determine the cloud point of the oil sample quickly and exactly.

FIG. 3 shows the measuring vessel according to the invention in an apparatus for cloud point determination. Reference number 1 in the figure indicates the measuring vessel generally. The measuring vessel 1 comprises cooling jacket 2, 3, which consists of upper part 2 and bottom part 3, temperature indicator 4, measuring space 5, oil sample exit channel 6, cooling liquid supply channel 7, oil sample supply channel 8, input 9 for the temperature indicator, connection 10 for the temperature indicator and cooling liquid exit channel 11.

FIG. 4 shows an alternative measuring vessel according to the invention in an apparatus for cloud point determination. Reference number 1 in the figure indicates the measuring vessel generally. The measuring vessel 1 comprises cooling jacket 2, 3, which consists of upper pan 2 and bottom pan 3, temperature indicator 4, measuring space 5, oil sample exit channel 6, cooling liquid supply channel 7, oil sample supply channel 8, input 9 for the temperature indicator, connection 10 for the temperature indicator and cooling liquid exit channel 11. In addition, the jacket of the measuring vessel has an annular part 12 located between the conical parts.

It is an essential feature of the measuring vessel according to the invention in an apparatus for cloud point determination that it is of such a shape that sufficient heat convection takes place in measuring space 5 in relation to the conduction taking place through the wall.

An advantageous shape for measuring vessel 1 is one shaped like oppositely located cones. Hereby the upper part 2 of the measuring vessel is shaped like a truncated cone, like the bottom part 3 of the measuring vessel, and these together form the measuring space 5.

An advantageous solid angle of apex point of the measuring vessel cones is 25°–100°, but a preferable value for the solid angle of apex point is 40°–60°.

The cones forming the measuring vessel may be of shales different from each other, whereby the upper part and bottom part of the cooling jacket have different angles of point, but in a preferable embodiment the measuring vessel consists of two similar cones.

The measuring vessel shown in FIGS. 3 and 4 has a jacket which may consist not only of pans shaped as circular cones but also of conical polygons, of a rotation ellipse or of a hemisphere.

The shape of the measuring vessel is partly dependent on the chosen raw material and on the available production technology. In some cases a measuring vessel shaped as a circular cone may be more easily manufactured than a measuring vessel formed by conical polygons, by a rotation ellipse or a hemisphere.

When using an apparatus according to the invention where the inner diameter of the measuring vessel was 55 mm and its height 110 mm the cloud point of oil could be measured from the process flow at intervals of approximately 10 minutes and the reproducibility of measurements was below 0.5° C.

We claim:

1. An apparatus for the determination of the cloud point of oil having a cooling jacket, a measuring space, a temperature indicator, wherein an oil sample in the measuring space is cooled with the aid of a cooling jacket surrounded by the measuring space and the cloud point is determined from a turning point on the oil cooling curve, wherein the measuring space is essentially shaped like two oppositely oriented hollow cones disposed to face each other flat base to base along a common bottom perimeter or circumference such that each apex points outwards along a mutual parallel axis of said two cones in an opposite direction, or two oppositely oriented hollow rotational semi-ellipsoids disposed to face each other flat base to base along a common bottom oval circumference where each rotational semi-ellipsoid has its rounded surface placed outwards along a mutual parallel axis of revolution said two ellipsoids in an opposite direction, and wherein the point of angle of each of the cones is 25°–100°.

2. The apparatus according to claim 1, wherein the measuring space is formed by two hollow circular cones disposed to face each other flat base to base along a common bottom circumference such that each apex points outwards along a mutual parallel axis of said two cones according to an opposite direction.

3. The apparatus according to claim 1 or 2, wherein the point of angle of each of the cones is 40°–60°.

4. The apparatus according to claim 1, wherein the cones or ellipsoids forming the measuring space are similar to one another in terms of material composition, material properties, geometric congruency and geometric dimensions.

\* \* \* \* \*